United States Patent [19]
Kalifa-Madar et al.

[11] Patent Number: 6,017,966
[45] Date of Patent: Jan. 25, 2000

[54] STABILIZED PHARMACEUTICAL COMPOSITIONS CONTAINING DOBUTAMINE

[75] Inventors: Daniéle Kalifa-Madar, Versailles; Francois Dietlin, Le Chesnay, both of France

[73] Assignee: Rhone-Poulenc Rorer SA, Anthony Cedex, France

[21] Appl. No.: 09/066,528

[22] Filed: Apr. 24, 1998

Related U.S. Application Data

[63] Continuation of application No. PCT/FR96/01671, Oct. 25, 1996.

[30] Foreign Application Priority Data

Oct. 27, 1995 [FR] France ..................................... 95 12688

[51] Int. Cl.⁷ ................................................. A61K 31/135
[52] U.S. Cl. ........................................... 514/654; 514/474
[58] Field of Search ..................... 514/474, 654

[56] References Cited

U.S. PATENT DOCUMENTS 3,808,317 4/1974 Hecht et al. .
3,966,905 6/1976 Nite .

FOREIGN PATENT DOCUMENTS

| 0 187 019 | 7/1986 | European Pat. Off. . |
| 2 231 377 | 12/1974 | France . |
| 2231796 | 9/1993 | United Kingdom . |
| WO94/13274 | 6/1994 | WIPO . |

OTHER PUBLICATIONS

Bishara et al., Dobutamine Hydrochloride, Analytical Profiles of Drug Substances, vol. 8, pp 139–158 (1979).

Springer, et al., Stabiliation of eye drops containg adrenaline, ACTA FAC. PHARM. UNIV., vol. 36 pp. 173–191 (1981).

Kirshenbaum et al., Stability of Dobutamine Hydrochloride in selected large volume parenterals, AM. J. HOSP. PHARM., vol. 39, No. 11, pp. 1923–1925 (1982).

Thoma K. et al., Stabilization of Adrenaline Solutions. 2. Report on the Stability fo Adrenaline Solutions, PHARMACT. Helv. vol. 61, No. 2, pp. 34–41 ( 1986).

Sucker H et al., Pharmaeutishche Technologie, THIEME VERLAG, P 215, TABLE 518 "1991".

*Primary Examiner*—Phyllis G. Spivack
*Attorney, Agent, or Firm*—Christine M. Hansen

[57] ABSTRACT

The present invention concerns stable injectable pharmaceutical compositions comprising dobutamine and ascorbic acid, or a salt thereof, and processes to prepare such compositions.

11 Claims, No Drawings

STABILIZED PHARMACEUTICAL COMPOSITIONS CONTAINING DOBUTAMINE

This is a continuation application of International Application No. PCT/FR96/01671, filed Oct. 25, 1996, published as WO97/15329 on May 1, 1997.

The present invention relates to novel dobutamine-based liquid formulations.

It is known, according to the article by Bishara R. H. and Long H. B. Dobutamine hydrochloride which appeared in Analytical Profiles of drug Substances, Academic Press (1979), volume 8, pages 139–158, that solutions of dobutamine in water are not stable, on the one hand, during heat sterilization and, on the other hand, during their preservation.

The degradation of dobutamine appears in the form of a pink color which gradually changes to grey and may even result in a precipitate. The degradation products are derivatives which have so far not been identified. Only the color of the solution makes it possible to detect their presence.

To solve this problem, it has long been known to stabilize the said solutions by adding sulphite to them. Thus, dobutamine is currently marketed in a ready-for-use liquid solution based on the following composition:

| | |
|---|---|
| dobutamine HCl | 280.2 mg |
| sodium metabisulphite | 4.5 mg |
| HCl or NaOH qs | pH 4.0 |
| water qs | 20 ml |

These solutions are then packaged under nitrogen to prevent as far as possible the oxidation of dobutamine during its preservation.

It is known that sulphites pose, in humans, drug control and toxicity problems.

The pharmaceutical industry has therefore for a long time been trying to prepare ready-for-use dobutamine solutions exhibiting sufficient stability criteria to allow heat-sterilization of the said solutions and/or their preservation for periods of several months, but free of sulphites.

The present invention has achieved this objective and relates to liquid pharmaceutical compositions containing dobutamine and ascorbic acid or one of its derivatives in a quantity sufficient to preserve the stability thereof.

The liquid pharmaceutical composition is preferably an aqueous injectable composition. The preferred ascorbic acid derivative which is used in these compositions is sodium ascorbate.

The quantity of ascorbic acid or of ascorbic acid derivative which is used by weight is preferably greater than 1% relative to dobutamine and still more preferably between 1.5 and 90%. It is evident that higher quantities could be used since this derivative is not toxic for humans, but since ascorbic acid or its derivative are used to stabilize dobutamine, quantities sufficient to maintain stability are preferred.

Thus, quantities by weight which are even more limited and situated between 2 and 20% of ascorbic acid or of one of its derivatives per 100 g of dobutamine are sufficient to meet this objective; the use of quantities by weight of between 3.5 and 10% is most particularly preferred.

As the stability of dobutamine and ascorbic acid or its derivative vary with the nature of the pH, it is recommended to maintain the pH of the solution in acidic form. Thus, a pH of the said solution of between 4 and 7 is preferred. Below pH 4, the solutions can hardly be used for a use by the injectable route. Above pH 7, dobutamine is not stable. It is thus clearly expressed under the preparation conditions as described, for example, in the VIDAL dictionary not to mix solutions of dobutamine with 5% solutions of sodium bicarbonate or highly alkaline solutions.

The preferred solutions according to the invention will be set at a pH close to 5.5. In the case where the pH is set at about 5.5, quantities by weight of sodium ascorbate, calculated relative to dobutamine, of between 1 and 3% are sufficient to stabilize dobutamine during sterilization. It is thus advantageous to add a pH-stabilizing agent, such as sodium monohydrogen phosphate, to the solution of dobutamine and ascorbic acid or one of its derivatives.

The composition thus prepared can be sterilized by heat treatment, for example at 120° C. for a few minutes or by sterilizing filtration.

The preferred composition according to the invention has the following composition:

| | |
|---|---|
| dobutamine hydrochloride | 280.2 mg |
| Na$_2$HPO$_4$ | 150 mg |
| Sodium ascorbate | 25 mg |
| HCl IN qs | pH 5.5 |
| water qs | 20 ml |

1st COMPARATIVE TRIAL

Protocol

The first trial was carried out with a composition identical to that of Dobutrex® dobutamine hydrochloride injection sold by Eli Lilly and Company but without sulphite:

| | |
|---|---|
| Dobutamine.HCl | 280.2 mg |
| HCl or NaOH QS | pH 4.0 |
| water for injection QS | 20 ml |
| nitrogen QS | |

Results:

The product breaks down in heat. It is converted to a grey precipitate during sterilization.

2nd COMPARATIVE TRIAL

Protocol:

The composition is identical to that of Dobutrex® but without sulphite; the solution is sterilized by filtration.

| | |
|---|---|
| Dobutamine.HCl | 280.2 mg |
| HCl or NaOH QS | pH 4.0 |
| water for injection QS | 20 ml |
| nitrogen QS | |

Results:

The product is not stable. Immediately after manufacture, the dobutamine.HCl content is 268 mg/20 ml for a lower limit of 266 mg/20 ml. After 1 month of storage at room temperature, a pink color or a grey precipitate appears.

3rd TRIAL

Aim:

To manufacture a solution containing sulphite, sterilized by filtration or using heat.

Protocol:

The composition is identical to that of Dobutrex®:

| | |
|---|---|
| Dobutamine.HCl | 280.2 mg |
| Sodium metabisulphite | 4.5 mg |
| HCl or NaOH QS | pH 4.0 |
| water for injection QS | 20 ml |
| nitrogen QS | |

A portion of the batch was autoclaved at 121° C. for 20 minutes (277 bottles), which gave batch A. The other, non-autoclaved portion (592 bottles) constituted batch B. The batches are preserved at 25° C., 40° C. and 50° C.

Results:

After manufacture, batch A has a slight pale yellow color. Both batches are not stable; the sulphites are used up during manufacture and preservation, as shown by the values presented in the table below.

| PRODUCT | TIME/TEMPERATURE | PERCENTAGE OF $SO_2$ |
|---|---|---|
| Dobutrex - commercial batch | | 2.56 |
| Trial A | Time O | 1.16 |
| | 1 month/25° C. | 0.49 |
| | 1 month/40° C. | 0.00 |
| | 1 month/50° C. | 0.00 |
| Trial B | Time O | 1.60 |
| | 1 month/25° C. | 0.70 |
| | 1 month/40° C. | 0.40 |
| | 1 month/50° C. | 0.00 |

For both batches, after 3 months of storage at 25° C., the solutions have a pink color and a grey precipitate. The Dobutamine content remains, nevertheless, within the limits of ±5 per cent of the theoretical value.

1st TRIAL ACCORDING TO THE INVENTION

Solutions with sodium ascorbate with pH variation.

Protocol:

The solution is prepared by adding a quantity of sodium ascorbate (19 ml of a solution at 0.05–0.10 or 0.15 per cent, per 20 ml of finished product) and by varying the pH (3.5–4.0 or 4.5). There is no sulphite.

The solutions are prepared under nitrogen and autoclaved at 121° C./20 minutes.

The solutions are analyzed after sterilization and they are preserved at 50° C.

Results:

Immediately After Heat-sterilization:

there is no heat-degradation of dobutamine, the chromatographic profile shows secondary peaks whose size increases with the quantity of ascorbate provided, for the same pH value. The size of these peaks decreases from pH 3.5 to 4.5, the yellow color increases with the quantity of ascorbate provided, for the same pH. This color decreases from pH 3.5 to 4.5.

After 1 and a Half Months at 50° C.:

The values are collated in the table below.

| Concentration of ascorbate in the final solution | initial pH | Absorbance at 308 nm* | Dobutamine (% of the initial value) | % of the secondary peaks (ratio of the surface areas) |
|---|---|---|---|---|
| 0.1425% | 3.5 | 2.6910 | 98 | 4.68 |
| | 4.0 | 1.1669 | 100 | 2.47 |
| | 4.5 | 0.6230 | 102 | 0.43 |
| 0.095% | 3.5 | 2.4669 | 98 | 2.44 |
| | 4.0 | 0.9400 | 99 | 1.36 |
| | 4.5 | 0.8960 | 96 | 0.78 |
| 0.0475% | 3.5 | Cloudy | 103 | 2.29 |
| | 4.0 | Cloudy | 103 | 0.93 |
| | 4.5 | Cloudy | 103 | 0.24 |

*of the solution against the non-autoclaved solution.

The solutions manufactured with 0.0475 per cent of ascorbate are not stable. pH 4.5 gives the best results. With this pH, the color and the secondary peaks are the lowest 2nd TRIAL ACCORDING TO THE INVENTION The variation of the quantity of ascorbate added was studied at a pH set at 4.5.

Solutions are prepared with the following sodium ascorbate concentrations: 45; 54; 63; 72; 81; 90; 135; 271 mg per 100 ml of final solution from 19 ml of sodium ascorbate solutions at the following concentrations: 48; 57; 67; 76; 86; 95; 142; 285 mg per 100 ml which are adjusted to 20 ml.

The solutions are prepared under nitrogen and autoclaved at 120° C./20 minutes.

The solutions are analyzed after sterilization.

| Concentration of ascorbate in the solution % | pH after sterilization | Absorbance at 308 nm* | Dobutamine content (g/100 ml) | sum of the secondary peaks |
|---|---|---|---|---|
| 0.045 | 4.9 | 0.618 | 1.43 | 0.98 |
| 0.054 | 4.9 | 0.471 | 1.46 | 0.63 |
| 0.063 | 4.7 | 0.584 | 1.47 | 0.74 |
| 0.072 | 4.7 | 0.569 | 1.47 | 0.70 |
| 0.081 | 4.7 | 0.594 | 1.46 | 0.72 |
| 0.090 | 4.7 | 0.710 | 1.48 | 0.92 |
| 0.135 | 4.6 | 0.804 | 1.50 | 0.95 |
| 0.271 | 4.6 | 1.136 | 1.44 | 1.46 |

The minimum concentration of sodium ascorbate at pH 4.5 which protects dobutamine is about 54 mg/100 ml, which corresponds to a weight ratio relative to dobutamine of about 3.8%.

The non-sterilized solutions maintained in the air are pink in 24 hours, except for ascorbate concentrations of 135 and 271 mg/100 ml. The 135 mg/100 ml concentration is the minimum concentration which makes it possible to protect dobutamine for 24 hours after opening the bottle, the solution remaining in the open air. This concentration corresponds to a weight ratio relative to dobutamine of 9.6%.

3rd TRIAL ACCORDING TO THE INVENTION

Aim:

To optimize stability by varying the pH

Protocol:

The solutions are all manufactured with a sodium ascorbate concentration per 100 ml of solution of 0.135%.

The pH is adjusted to 4.5-5.0-5.5-6.0-6.5-7.0 with hydrochloric acid.

There is no sulphite.

The manufacture is carried out under nitrogen.

The bottles are sterilized at 120° C.C/20 minutes.

Results:

Immediately After Heat-sterilization:

dobutamine is heat-stable, the color decreases from pH 4.5 to 5.5 and then increases with the pH, the secondary peaks (resulting from ascorbate) decrease from pH 4.5 to 5.5.

| Initial pH | Absorbance at 308 nm* | Dobutamine.HCl (g/100 ml) | Sum of the secondary peaks |
|---|---|---|---|
| 4.5 | 0.823 | 1.46 | 1.19 |
| 5.0 | 0.691 | 1.44 | 0.56 |
| 5.5 | 0.644 | 1.45 | 0.37 |
| 6.0 | 0.741 | 1.45 | 0.35 |
| 6.5 | 0.762 | 1.43 | 0.36 |
| 7.0 | 0.895 | 1.51 | 0.33 |

*of the solution diluted ½ against water

A minimum absorbance of the solution is obtained with a pH of 5.5. The dobutamine content is not affected by the variation in pH in the range studied.

After One Month at 50° C.

dobutamine is stable, the secondary peaks (resulting from ascorbate) decrease from pH 4.5 to 5.5. At pH 5.5, their sum is 0.11 per cent.

| Initial pH | Dobutamine (percentage of the initial content) | Percentage of the secondary peaks | Absorbance at 308 nm* |
| --- | --- | --- | --- |
| 4.5 | 100 | 0.97 | 1.033 |
| 5.0 | 100 | 0.32 | 0.572 |
| 5.5 | 99 | 0.11 | 0.313 |

*of the solution diluted ½ against water.

4th TRIAL ACCORDING TO THE INVENTION

Aim: to optimize the minimum quantity of sodium ascorbate as a function of the pH.

Operating Protocol

| dobutamine.HCl | 1.4 | 1.4 | 1.4 | 1.4 | 1.4 | 1.4 | 1.4 | 1.4 |
| --- | --- | --- | --- | --- | --- | --- | --- | --- |
| Na ascorbate (0.0480 g/100 ml) | 95 ml | 95 ml | | | | | | |
| Na ascorbate (0.0383 g/100 ml) | | | 95 ml | 95 ml | | | | |
| Na ascorbate (0.0292 g/100 ml) | | | | | 95 ml | 95 ml | | |
| Na ascorbate (0.0106 g/100 ml) | | | | | | | 95 ml | 95 ml |
| HCl 0.1 N or NaOH 0.1 N QS | pH 5.5 | pH 6.5 | pH 5.5 | pH 6.5 | pH 5.5 | pH 6.5 | pH 5.5 | pH 6.5 |
| H$_2$O QS | 100 ml | 100 ml | 100 ml | 100 ml | 100 ml | 100 ml | 100 ml | 100 ml |

Preparations sterilized under nitrogen 120° C./20 min

Results

| Concentration of sodium ascorbate (g/100 ml) | pH before sterilization | pH after sterilization | Absorbance at 308 nm* | Dobutamine.HCl content | Sum of the secondary peaks |
| --- | --- | --- | --- | --- | --- |
| 0.0456 | 5.5 | 5.9 | 0.383 | 1.4 | 0.06 |
| | 6.5 | 6.4 | 0.405 | 1.4 | 0.03 |
| 0.0364 | 5.5 | 5.8 | 0.326 | No significant | 0.04 |
| | 6.5 | 6.3 | 0.355 | variation | 0.03 |
| 0.0277 | 5.5 | 5.7 | 0.238 | | 0.05 |
| | 6.5 | 6.3 | 0.317 | | 0.02 |
| 0.0101 | 5.5 | 5.8 | 0.252 | | 0.02 |
| | 6.5 | 6.4 | 0.340 | | 0.03 |
| 0 | 5.5 | 3.99 | 0.635 | Not determined | |
| | 6.5 | 6.21 | 0.909 | | |

*of the solution diluted one half against water

5th TRIAL ACCORDING TO THE INVENTION

Aim:

To stabilize the pH.

Protocol:

Given the results obtained in Trial 3 according to the invention, a pH 5.5 value is selected. To stabilize the pH, disodium phosphate is added. The optimum quantity is determined by judging the buffer effect of solutions with varying concentrations of disodium phosphate.

Results:

The buffer effect is maximum at a concentration of 150 mg/20 ml

6th TRIAL ACCORDING TO THE INVENTION

Aim:

To predict the extent of the formation of secondary peaks during preservation, by increasing the content of ascorbate. It is possible to envisage the fact that less concentrated solutions will in the long run have secondary peaks whose size will be at most equal to that determined during this trial.

Protocol:

The solution is prepared according to the following formulation:

| | |
| --- | --- |
| Dobutamine.HCl | 280.2 mg |
| NaHPO$_4$·2H$_2$O | 150 mg |
| Sodium ascorbate | 250 mg (weight ratio/dobutamine = 89%) |
| HCl 1N QS | pH 5.5 |
| Water for injection QS | 20 ml |
| nitrogen QS | |

The ascorbate is provided at a concentration approximately 10 times greater than that chosen for trial 3. The solution is preserved at 25° C. and 40° C. for 6 months.

A portion of the solutions was heat-sterilized:

121° C./20 minutes

124° C./10 minutes

125° C./8 minutes

126° C./6 minutes

Results:

All the heat-sterilized solutions are yellow but the dobutamine content remains unchanged.

For the non-autoclaved solutions:

dobutamine is stable at 25° C. but it decreases at 40° C.

ascorbic acid is stable at 25° C. but it decreases at 40° C.

disodium phosphate makes it possible to stabilize the pH, the color increases only at 40° C., after 6 months, the secondary peaks (resulting from ascorbate) represent 0.79 per cent at 25° C. and 2.14 per cent at 40° C.

The results, after 6 months of storage, are collated in the table below.

| Temperatures | pH | Dobutamine (% initial content) | % of the secondary peaks | Content of ascorbate (%) | Absorbance at 308 nm* |
|---|---|---|---|---|---|
| 25° C. | 5.5 | 100 | 0.79 | 1.13 | 2.53 |
| 40° C. | 5.7 | 100 | 2.14 | 0.98 | 2.99 |

*of the solution diluted ½ against water

The following formulation may be selected:

| | |
|---|---|
| Dobutamine.HCl | 280.2 mg |
| NaHPO$_4$·2H$_2$O | 150 mg |
| Sodium ascorbate | 27 mg |
| HCl 1N QS | pH 5.5 |
| Water for injection QS | 20 ml |
| nitrogen QS | |

Immediately before sterilization, the absorbance of the solution (dilution one half against water) at 308 nm is 0.54. After sterilization, it is 0.64. This small increase shows the good heat-stability of the preparation. It is, however, possible to dispense with heat-sterilization in favour of a preparation under aseptic conditions with double sterilizing filtration.

We claim:

1. An injectable pharmaceutical composition comprising dobutamine and ascorbic acid or a salt thereof.
2. The composition of claim 1, wherein the dobutamine is essentially stable after one month of storage at 50° C. or after heat sterilization.
3. The composition of claim 2, wherein the ascorbic acid or the salt thereof, is present in an amount greater than 1% by weight of the dobutamine.
4. The composition of claim 3, wherein the ascorbic acid or the salt thereof, is present in an amount between 1.5 and 90% by weight of the dobutamine.
5. The composition of claim 4, wherein the ascorbic acid or the salt thereof, is present in an amount between 2 and 20% by weight of the dobutamine.
6. The composition of claim 5, wherein the ascorbic acid or the salt thereof, is present in an amount between 3.5 and 10% by weight of the dobutamine.
7. The composition of claim 3 having a pH of between 4 and 7.
8. The composition of claim 7, wherein the pH is about 5.5.
9. The composition of claim 1 that is sterilized by heat treatment or by sterilizing filtration.
10. A process for the preparation of an injectable dobutamine solution comprising combining dobutamine and ascorbic acid or a salt thereof in a solvent.
11. The process of claim 10 wherein ascorbic acid or a salt thereof is present in an amount between 3.5 and 10% by weight of the dobutamine and the solvent is water.

* * * * *